(12) United States Patent
Boer et al.

(10) Patent No.: US 12,005,275 B2
(45) Date of Patent: Jun. 11, 2024

(54) METHOD AND SYSTEM FOR ULTRASOUND INDUCED HYPERTHERMIA WITH MICROWAVE THERMOMETRY FEEDBACK

(71) Applicant: Sonify Biosciences, LLC, Baltimore, MD (US)

(72) Inventors: Miriam Sara Boer, Baltimore, MD (US); Daniel Jordan Rogers, Baltimore, MD (US)

(73) Assignee: Sonify Biosciences, LLC, Baltimore, MD (US)

( * ) Notice: Subject to any disclaimer, the term of this patent is extended or adjusted under 35 U.S.C. 154(b) by 0 days.

(21) Appl. No.: 18/129,817

(22) Filed: Mar. 31, 2023

(65) Prior Publication Data

US 2023/0233879 A1    Jul. 27, 2023

Related U.S. Application Data

(63) Continuation of application No. 17/466,789, filed on Sep. 3, 2021, now abandoned, which is a continuation
(Continued)

(51) Int. Cl.
*A61N 7/02* (2006.01)
*A61B 5/00* (2006.01)
(Continued)

(52) U.S. Cl.
CPC ............ *A61N 7/02* (2013.01); *A61B 5/01* (2013.01); *A61B 5/0507* (2013.01);
(Continued)

(58) Field of Classification Search
CPC . A61N 7/02; A61N 1/403; A61N 5/02; A61N 5/022; A61N 5/025; A61B 5/01;
(Continued)

(56) References Cited

U.S. PATENT DOCUMENTS 4,889,122 A    12/1989  Watmough
5,344,435 A    9/1994   Turner
(Continued)

FOREIGN PATENT DOCUMENTS

WO    WO 1993/000132 A1    1/1993
WO    WO 2015/077006 A1    5/2015

OTHER PUBLICATIONS

Arunachalam et al. "Characterization of a Digital Microwave Radiometry System for Noninvasive Thermometry Using a Temperature-Controlled Homogeneous Test Load," Phys Med Biol. 2008; 53(14): 3883-3901) (Year: 2008) (20 pages).
(Continued)

*Primary Examiner* — Hien N Nguyen
(74) *Attorney, Agent, or Firm* — Nixon Peabody LLP

(57) ABSTRACT

A device for providing hyperthermia treatment includes an ultrasound energy generator configured to apply low intensity ultrasound to target tissue. The low intensity ultrasound energy induces therapeutic heating in the tissue at or below the surface of the skin. In order to control the temperature of the tissue during therapy, a microwave radiometer, such as a Dicke radiometer, can be used to measure the temperature of the tissue and feed back the temperature measurement to the ultrasound energy generator to control ultrasonic energy produced and control the temperature of the target tissue.

10 Claims, 2 Drawing Sheets

Related U.S. Application Data of application No. 16/324,702, filed as application No. PCT/US2017/046530 on Aug. 11, 2017, now abandoned.

(60) Provisional application No. 62/373,609, filed on Aug. 11, 2016.

(51) Int. Cl.

| | | |
|---|---|---|
| *A61B 5/01* | (2006.01) | |
| *A61B 5/0507* | (2021.01) | |
| *A61B 18/00* | (2006.01) | |
| *A61B 18/04* | (2006.01) | |
| *A61K 41/00* | (2020.01) | |
| *A61N 1/40* | (2006.01) | |
| *A61N 5/02* | (2006.01) | |

(52) U.S. Cl.
CPC ............ *A61B 5/4836* (2013.01); *A61B 18/04* (2013.01); *A61K 41/0052* (2013.01); *A61N 1/403* (2013.01); *A61N 5/02* (2013.01); *A61N 5/022* (2013.01); *A61N 5/025* (2013.01); *A61B 2018/00791* (2013.01)

(58) Field of Classification Search
CPC ..... A61B 5/0507; A61B 5/4836; A61B 18/04; A61B 2018/00791; A61K 41/0052
See application file for complete search history.

(56) References Cited

U.S. PATENT DOCUMENTS

| | | | |
|---|---|---|---|
| 5,688,050 A * | 11/1997 | Sterzer | A61B 5/015 |
| | | | 374/E11.003 |
| 2009/0051529 A1* | 2/2009 | Tsuji | G01S 13/38 |
| | | | 340/554 |
| 2010/0025453 A1* | 2/2010 | Geissler | B23K 20/005 |
| | | | 228/103 |
| 2010/0069782 A1* | 3/2010 | Icove | G01K 11/006 |
| | | | 600/549 |
| 2011/0087096 A1 | 4/2011 | Behar | |
| 2012/0108918 A1* | 5/2012 | Jarvik | A61B 5/4824 |
| | | | 600/301 |
| 2013/0096595 A1* | 4/2013 | Myhr | A61N 7/022 |
| | | | 606/169 |
| 2014/0336665 A1* | 11/2014 | Gavala | A61B 17/22012 |
| | | | 606/128 |

OTHER PUBLICATIONS

International Search Report and Written Opinion of International Searching Authority for International Patent Application No. PCT/US2017/046530, dated Nov. 13, 2017 (6 pages).

* cited by examiner

METHOD AND SYSTEM FOR ULTRASOUND INDUCED HYPERTHERMIA WITH MICROWAVE THERMOMETRY FEEDBACK

CROSS-REFERENCE TO RELATED APPLICATIONS

This application is a continuation of U.S. patent application Ser. No. 17/466,789, filed on Sep. 3, 2021, which is a continuation of U.S. patent application Ser. No. 16/324,702, filed on Feb. 11, 2019, which is a 35 U.S.C. § 371 National Phase Entry Application of International Application No. PCT/US2017/046530 filed Aug. 11, 2017, which claims benefit under 35 U.S.C. § 119(e) of U.S. Provisional Application No. 62/373,609, filed on Aug. 11, 2016, the contents of which are hereby incorporated by reference herein in their entireties.

STATEMENT REGARDING FEDERALLY SPONSORED RESEARCH

Not Applicable.

REFERENCE TO MICROFICHE APPENDIX

Not Applicable

BACKGROUND

Technical Field of the Invention

The present invention is directed to the use of low intensity ultrasound for inducing hyperthermia for the treatment of biological tissue and the use of passive microwave radiometry for sensing temperature of the tissue. More specifically, the present invention is directed to using the passive microwave radiometry to control biological treatment temperatures in hyperthermia treatment systems.

Description of the Prior Art

Despite the rates of many cancers decreasing, the search for effective treatments is ongoing, especially for cancers that are increasing in occurrence and mortality. As the scientific and medical communities' knowledge increases and becomes more nuanced, a multi-pronged treatment approach is often embraced. One frequently used therapeutic component is hyperthermia, the gentle non-burning heating of affected tissue. Hyperthermia is often paired with other therapies as an adjuvant. Currently, heat is delivered via microwave energy, and temperature is monitored via either treating the patient in an MRI machine or placing thermocouples externally or in the nearest bodily orifice to get as close to the treatment site as possible. While this treatment plays an important part in a cancer patient's care, there are drawbacks to the current approach.

SUMMARY

The present invention is directed to methods and systems that deliver heat through the use of ultrasound, not microwaves. There are two primary reasons why this is preferable. The first is the patient experience; while microwaves are non-ionizing radiation, the idea of being microwaved is not a pleasant one for the patient. The second is that microwaves create an electromagnetic field that disrupts certain electronics. With this disruptive electromagnetic field, the scope of possible temperature feedback mechanisms and systems is limited. Ultrasound is not electromagnetic radiation and so does not create this disruptive field. Thus, ultrasound based hyperthermia therapy systems according to embodiments of the present invention can utilize the capabilities of passive microwave thermo-sensing. In accordance with some embodiments of the invention, remote passive microwave thermo-sensing can be integrated with the ultrasound heat delivery system to provide remote focused temperature feedback control from 0-2 cm below the skin surface. This system can provide controlled and focused heat delivery at a substantially lower cost than current systems that use MRI based temperature monitoring and unlike an MRI based system, systems according to the present invention will not require special shielding or facilities to function and can be much smaller.

In accordance with some embodiments of the invention, the hyperthermia therapy system can include an ultrasound transducer for delivering low intensity ultrasound signals to heat to a given volume of tissue via ultrasonic energy, and the administration of this ultrasonic energy and the resulting heat therapy can be controlled using feedback from a passive microwave radiometry based temperature sensor.

In accordance with some embodiments of the invention, the system can induce hyperthermia—a gentle non-ablative heating of tissue using ultrasound. The devices and systems according to the invention can be used to treat maladies below the surface of the skin, such as melanoma, basal carcinoma, squamous carcinoma, and other superficial tumors. In accordance with some embodiments of the invention, the devices and systems can be used as part of an adjuvant treatment for these and other maladies. In accordance with some embodiments of the invention, during treatment, the tissue temperature can be raised and held for the duration of treatment to a predefined temperature or temperature range (e.g., between 38-44 C, although other ranges are possible). The set point treatment temperature can have an accuracy of +/−0.5-1.0 degree Celsius or better. The device will be intended for both laboratory and clinical use.

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

DETAILED DESCRIPTION OF PREFERRED EMBODIMENTS

The present invention is directed to methods and systems for using ultrasonic energy for hyperthermia therapies that produce non-ablative heating of tissue. In accordance with some embodiments of the invention, an ultrasound signal generator drives an ultrasound transducer to produce low intensity ultrasonic energy that can be applied to a treatment site in tissue. The low intensity ultrasonic energy induces heating and raises the temperature of the tissue at the treatment site. In accordance with some embodiments of the invention, a microwave radiometer can be aimed at the treatment site and used to determine the temperature of the tissue at the treatment site by measuring the microwave energy received from the treatment site. The temperature determined by the radiometer can be fed back into the ultrasound generator to control the ultrasonic energy applied to the treatment site to adjust and maintain the temperature of treatment site according to a predefined temperature.

When the ultrasound signal is applied to treatment site in tissue, the ultrasonic energy induces heating. The amount of heating is in part a function of the density of the tissue in the treatment site and physiologic composition of the tissue, such as water and fat content. In addition, the density and physiologic composition of the tissue can change during the course of treatment resulting in temperature variations that can limit the effectiveness of the hyperthermia therapy. Thus, it is desirable to be able to determine the temperature of tissue at the treatment site during the course of the therapy and to control the application of ultrasound energy as required to maintain the desired temperature for the specified therapy. In accordance with some embodiments of the invention, it can be desirable to maintain a constant temperature or temperature range (e.g., 41° C. or 38-44° C.) over at least part of the course of treatment. In accordance with some embodiments of the invention, it can be desirable to apply temperature profile (e.g., the temperature changes with time according to a plan or program) over at least part of the course of treatment.

Figure 1:
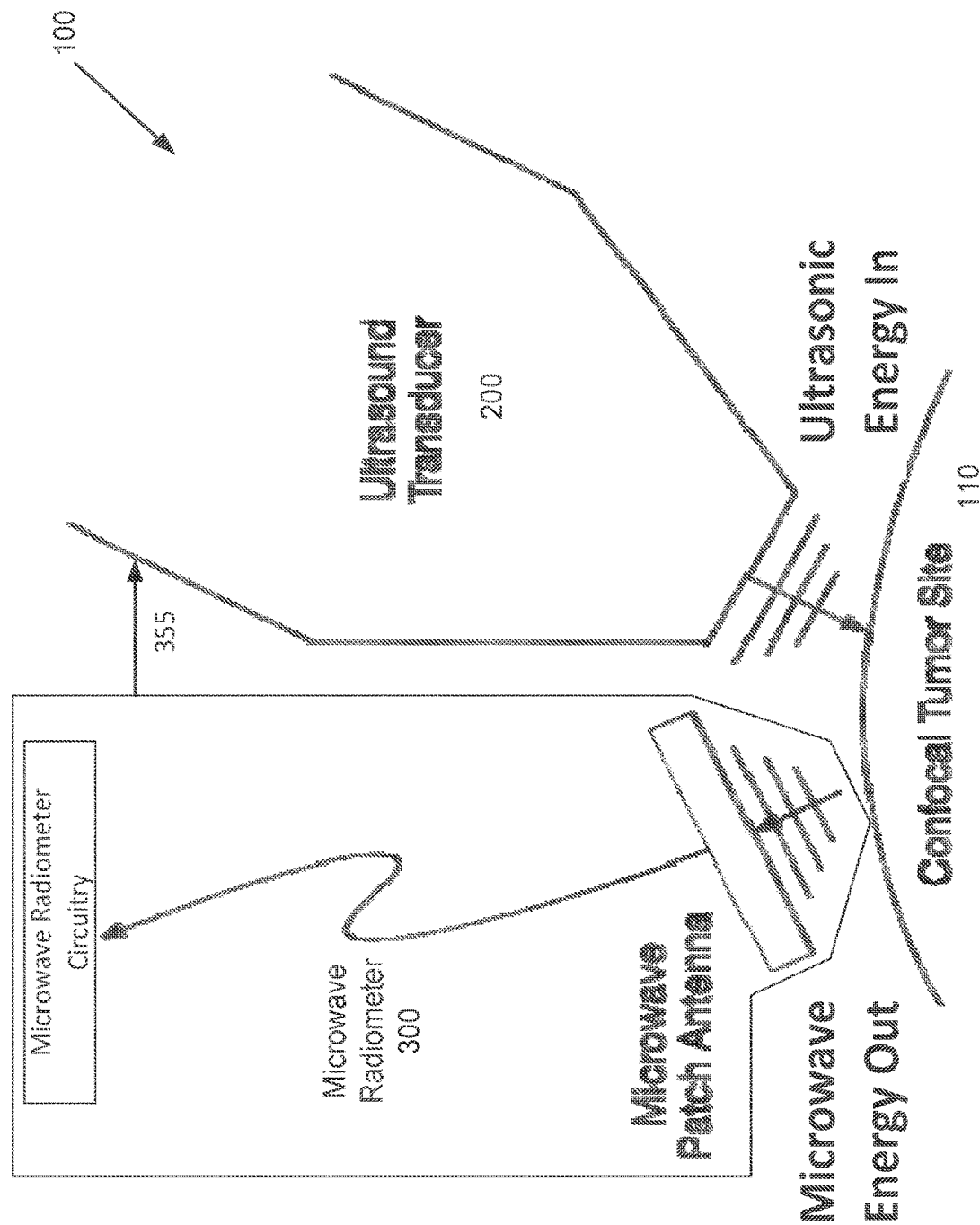
FIG. 1 is a diagrammatic view of an ultrasound based hyperthermia treatment system according to some embodiments of the invention.

FIG. 1 shows a diagrammatic view of an ultrasound hyperthermia system 100 according to some embodiments of the invention. The ultrasound hyperthermia system 100 includes a controllable ultrasound energy source 200 and a microwave radiometer 300. The ultrasound energy source 200 produces ultrasonic energy at a predefined frequency (e.g. 0.5-5.0 MHz) and a predefined intensity (e.g., 0.1-3.0 W/cm$^2$) to induce heating of tissue at a target site 110 on the skin surface and at least 2.0 cm below the skin surface. The ultrasound energy source 200 can be controlled by an input signal to control the frequency and the intensity to regulate the heating induced in the target site 110. The ultrasonic energy can be increased to increase the temperature at the target site 110 and the ultrasonic energy can be decreased to decrease the temperature at the target site 110.

The microwave radiometer 300 measures the microwave energy emanating from the tissue at the treatment site 110 and uses the measured microwave energy to determine the temperature of the tissue at the treatment site 110. The temperature determined by the microwave radiometer can be fed back 355 to the ultrasound energy source 200 and used to control the output of the ultrasound generator and the ultrasound transducer to control the temperature induced by the ultrasound energy. In accordance with some embodiments of the invention, the set point temperature can be controlled to an accuracy of +/−0.5-1.0° C. or better.

In operation, the ultrasound energy source 200 can be configured to generate a predefined frequency and intensity of ultrasound energy that is applied to induce heating of tissue at the target site 110 and is expected to bring the tissue to a predefined temperature. While the ultrasound energy is being applied, the microwave radiometer is determining the temperature of the tissue at the target site 110 and sending the temperature values (and/or a signal 355 determined as function of the temperature values) to the ultrasound energy source 200. The ultrasound energy source 200 uses the temperature values (and/or the signal 355) to adjust the frequency and/or intensity of the ultrasound energy as it is being applied to the tissue at the target site 110 to raise or lower the tissue temperature to the predefined value or range.

Figure 2:
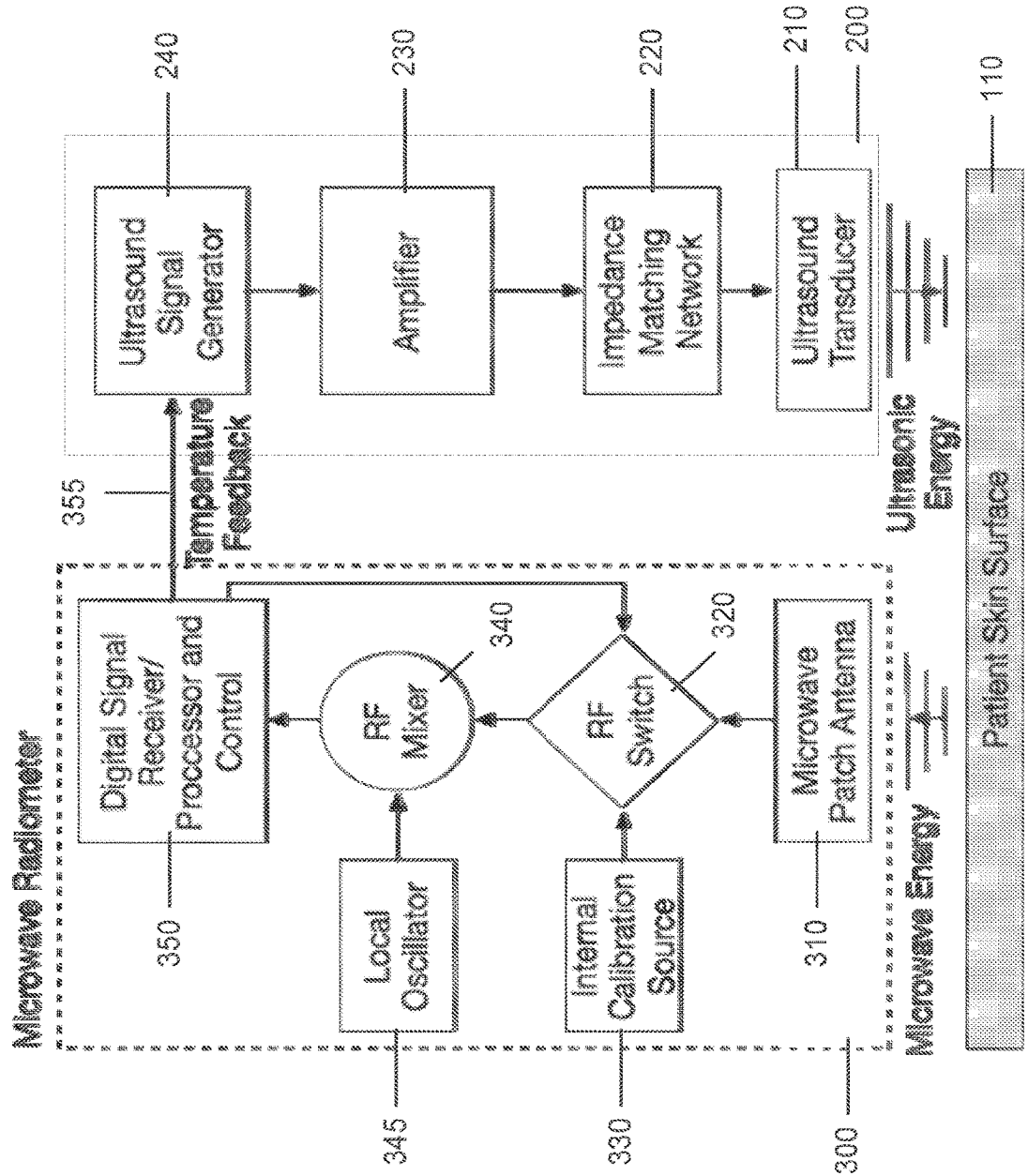
FIG. 2 is a more detailed diagrammatic view of an ultrasound based hyperthermia treatment system according to some embodiments of the invention.

FIG. 2 shows a more detailed diagrammatic view of an ultrasound hyperthermia system 100 according to some embodiments of the invention. In accordance with some embodiments of the invention, the ultrasound energy source 200 can include an ultrasound generator 240 coupled through an amplifier 230 and an impedance matching network 220 to an ultrasound transducer 210. The ultrasound generator 240 can be used to generate an arbitrary ultrasound waveform with an adjustable amplitude at frequency in the range, for example, from 0.5-5.0 MHz. In accordance with some embodiments of the invention, the ultrasound generator 240 can be, for example, an Agilent 3320 ultrasound generator. Depending on the desired level ultrasound energy and heating, the ultrasound signal can be amplified, for example, using an ENI 550L RF amplifier. The amplified ultrasound signal can be input into a piezoelectric ultrasound transducer to produce that ultrasound energy that can be applied to the tissue in the target site. Depending on the design of the amplifier and the ultrasound transducer, an impedance matching network can be used to couple the amplifier and transducer to match the capacitive loads of those components to maximize the power transfer through the system. In accordance with some embodiments of the invention, the ultrasonic transducer can be coupled via a recirculating, chilled water-filled cone through a sterile membrane to the patient tissue. The recirculating water can be chilled, for example, using an Oasis 170 pump/chiller, and can also be degassed using, for example, a Liqui-Cel membrane contactor 4×8 inline degasser, in order to remove any gas bubbles that may inhibit good coupling of the ultrasonic energy to the patient tissue. The sterile membrane can be disposable to prevent the spread of disease by the system that is in contact with patient tissue.

According to some embodiments of the invention, the water filled cone can act as a lens to control the focus of the ultrasound energy and different water filled cone configurations can be used to produce the desired ultrasound energy distribution to accommodate the dimensions of the target site.

In accordance with some embodiments of the invention, the microwave sensor can be focused on the volume of tissue being heated by the ultrasound transducer and can detect an emanating signal in the range from about 1 and 6 GHz. The microwave radiometer 300 includes a microwave antenna 310 and, for example, can be constructed based on the architecture of a Dicke Radiometer. The microwave radiometer 300 can include an internal calibrated resistor or other calibrated temperature source 330 that is used to determine an absolute temperature. The microwave radiometer 300 detects the temperature of the tissue relative to that of the calibrated temperature source using the RF switch 320. The ambient microwave background noise in the received microwave signal can be filtered and mixed down using the RF mixer 340 that is connected to a local oscillator 345 (e.g., that can be configured to produce a reference signal from 1 and 6 GHz) to produce a baseband signal. The baseband signal can be integrated for a period of time to determine the baseband energy of the measure microwave signal. This energy is proportional to the temperature, or thermal noise, detected by the antenna and compared to the calibrated internal source in order to determine the actual temperature.

In accordance with some of the embodiments of the invention, the microwave radiometer determines a measure of the temperature of the tissue as it is exposed to the ultrasonic energy. The measure of temperature provided by the microwave radiometer can be fed back 355 by the signal processor/controller 350 to the ultrasound generator 240 to adjust the level (e.g., signal frequency and intensity) of ultrasound output. In accordance with some embodiments, a control loop, such as a PID controller, can be used to control ultrasound energy output in order to maintain the temperature in the ultrasound focal volume at the required temperature for hyperthermia.

The microwave radiometer can include a signal processor/controller 350 that processes the baseband signal to determine the temperature of the tissue. The signal processor/controller 350 can include one or more digital signal processors and/or one or more microprocessors and associated memories for storing computer programs that can be used to process the baseband signal and determine the temperature of the tissue being treated.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. An ultrasound hyperthermia system comprising:
   a controllable ultrasound energy source producing ultrasonic energy at a predefined frequency in a range of 0.5-5.0 Megahertz (MHz) and a predefined intensity in a range of 0.1-3.0 Watts per cubic centimeter (W/cm$^2$), the ultrasonic energy inducing heating of a tissue at a target site to bring the tissue to a predefined temperature, the ultrasonic energy inducing the heating remotely from a source external surface of the controllable ultrasound energy source, a focal distance separating the source external surface and the target site, the controllable ultrasound energy source including
      an ultrasound generator configured to generate a low intensity ultrasound signal in a form of an arbitrary ultrasound waveform, the low intensity ultrasound signal inducing hyperthermia in the tissue for a treatment duration, the arbitrary ultrasound waveform having an adjustable amplitude at the predefined frequency,
      an amplifier communicatively coupled with the ultrasound generator and configured to amplify the ultrasound signal into an amplified ultrasound signal,
      an impedance matching network communicatively with the amplifier and configured to match capacitive loads of the amplified ultrasound signal for maximizing power transfer through the ultrasound hyperthermia system, and
      a piezoelectric ultrasound transducer communicatively coupled to the ultrasound generator via the impedance matching network, the piezoelectric ultrasound transducer producing the ultrasonic energy based on the amplified ultrasound signal;
   a water-filled cone coupling the piezoelectric ultrasound transducer, via a sterile membrane, to the tissue, the water-filled cone including recirculated and degassed chilled water, the water-filled cone focusing the ultrasonic energy to heat the tissue;
   a microwave radiometer for passively determining temperature of the tissue via received microwaves, the microwave radiometer having a radiometer external surface that is in contact with the target site, the microwave radiometer including
      a microwave antenna for detecting a microwave signal caused by the ultrasonic energy heating the tissue, the microwave antenna attached confocally to the controllable ultrasound energy source,
      an internal calibrated temperature source configured to determine an absolute temperature, and
      a Radio Frequency (RF) switch communicatively coupled with the microwave antenna and the internal calibrated temperature source, the RF switch being configured to detect, based on the microwave signal, a tissue temperature relative to the absolute temperature,
      a local oscillator configured to produce a baseband signal in a range of 1-6 Gigahertz (GHz),
      a Radio Frequency (RF) mixer communicatively coupled with the RF switch and the local oscillator, the RF mixer being configured to filter and mix down background noise in the microwave signal,
      a digital signal processor communicatively coupled with the RF mixer and RF switch, the digital signal processor configured to
         integrate the baseband signal for a period of time to determine a baseband energy of the microwave signal,
         determine an actual temperature by comparing the absolute temperature with the tissue temperature,
         feed back the actual temperature to the ultrasound generator, and
         adjust the predefined frequency and the predefined intensity from initial values to adjusted values within a respective ranges.

2. The ultrasound hyperthermia system of claim 1, further comprising a control loop communicatively coupled with the digital signal processor, the control loop configured to maintain the tissue temperature at a value required for achieving hyperthermia.

3. The ultrasound hyperthermia system of claim 2, wherein the control loop is a proportional-integral-derivative (PID) controller.

4. The ultrasound hyperthermia system of claim 1, wherein the ultrasonic transducer heats the target site of the tissue to a predefined site temperature in a range of 38-44 degrees Celsius.

5. The ultrasound hyperthermia system of claim 4, wherein the piezoelectric ultrasonic transducer heats a portion of the target site of the tissue at least 2.0 centimeters below a surface of the target site to a predefined sub-site temperature in a range of 38-44 degrees Celsius.

6. A method of providing ultrasound based heating to produce hyperthermia, the method comprising:
   generating, via an ultrasound generator, a low intensity ultrasound signal in a form of an arbitrary ultrasound waveform, the low intensity ultrasound signal inducing hyperthermia in a tissue for a treatment duration, the arbitrary ultrasound waveform having an adjustable amplitude at a predefined frequency in a range of 0.5-5.0 Megahertz (MHz);

amplifying, via an amplifier, the ultrasound signal into an amplified ultrasound signal;

matching, via an impedance matching network, capacitive loads of the amplified ultrasound signal for maximizing power transfer;

producing, via a piezoelectric ultrasound transducer, ultrasonic energy at the predefined frequency and a predefined intensity in a range of 0.1-3.0 Watts per cubic centimeter (W/cm$^2$);

based on the ultrasonic energy, inducing heating of the tissue at a target site to bring the tissue to a predefined temperature, the ultrasonic energy inducing the heating remotely from a source external surface of the piezoelectric ultrasound transducer, a focal distance separating the source external surface and the target site;

focusing the ultrasonic energy, via a water-filled cone, on the target site to heat the tissue;

recirculating and degassing chilled water flowing through the water-filled cone;

passively determining, via a microwave radiometer, temperature of the tissue via received microwaves, the microwave radiometer having a radiometer external surface that is in contact with the target site;

detecting, via a microwave antenna of the microwave radiometer, a microwave signal caused by the ultrasonic energy heating the tissue, the microwave antenna being attached confocally to the piezoelectric ultrasound transducer;

determining, via an internal calibrated temperature source of the microwave radiometer, an absolute temperature;

detecting, based on the microwave signal and via a Radio Frequency (RF) switch of the microwave radiometer, a tissue temperature relative to the absolute temperature;

producing, via a local oscillator of the microwave radiometer, a baseband signal of 1-6 Gigahertz (GHz);

filtering and mixing down, via a RF mixer of the microwave radiometer, background noise in the microwave signal;

integrating, via a digital signal processor of the microwave radiometer, the baseband signal for a period of time to determine a baseband energy of the microwave signal;

determining, via the digital signal processor, an actual temperature by comparing the absolute temperature with the tissue temperature;

feeding back, via the digital signal processor, the actual temperature to the ultrasound generator; and adjusting, via the digital signal processor, the predefined frequency and the predefined intensity from initial values to adjusted values within a respective ranges.

7. The method of claim 6, further comprising maintaining, via a control loop, the tissue temperature at a value required for achieving hyperthermia.

8. The method of claim 7, wherein the control loop is a proportional-integral-derivative (PID) controller.

9. The method of claim 6, further comprising the target site of the tissue to a predefined site temperature in a range of 38-44 degrees Celsius.

10. The method of claim 9, further comprising heating a portion of the target site of the tissue at least 2.0 centimeters below a surface of the target site to a predefined sub-site temperature in a range of 38-44 degrees Celsius.

* * * * *